United States Patent

Sheehy

Patent Number: 4,877,024
Date of Patent: Oct. 31, 1989

[54] AIRWAY

[75] Inventor: Patrick K. Sheehy, Reading, England

[73] Assignee: P K Airway Limited, Berkshire, England

[21] Appl. No.: 201,376

[22] PCT Filed: Jan. 18, 1985

[86] PCT No.: PCT/GB85/00023

§ 371 Date: Sep. 18, 1985

§ 102(e) Date: Sep. 18, 1985

[87] PCT Pub. No.: WO85/03232

PCT Pub. Date: Aug. 1, 1985

Related U.S. Application Data

[63] Continuation of Ser. No. 930,054, Nov. 12, 1986, abandoned, which is a continuation of Ser. No. 778,181, Sep. 18, 1985, abandoned.

[30] Foreign Application Priority Data

Jan. 18, 1984 [GB] United Kingdom ................. 8401324
Jan. 18, 1985 [WO] PCT Int'l Appl. ... PCT/GB85/00023

[51] Int. Cl.$^4$ ............................................. A61M 16/00
[52] U.S. Cl. ................................. 128/207.14; 604/284
[58] Field of Search ................................. 128/12–16, 128/200.26, 207.14, 206.29, 207.15, 207.17, 912, 202.28, 202.29, 861–863; 433/140, 93

[56] References Cited

U.S. PATENT DOCUMENTS

| | | |
|---|---|---|
| 1,498,810 | 6/1924 | Poe . |
| 2,036,218 | 4/1936 | Kammer .................. 604/27 |
| 2,669,988 | 2/1954 | Carpenter .................. 128/136 |
| 2,882,893 | 4/1959 | Godfroy .................. 128/136 |
| 3,039,469 | 6/1962 | Fountain .................. 128/207.17 |
| 3,756,244 | 9/1973 | Kinnear et al. .................. 128/207.14 |
| 4,112,936 | 9/1978 | Blachly . |
| 4,148,308 | 4/1979 | Sayer .................. 128/15 |
| 4,233,984 | 11/1980 | Walling .................. 128/207.14 |
| 4,256,099 | 3/1981 | Dryden .................. 128/200.26 |
| 4,270,531 | 6/1981 | Blachy et al. .................. 128/136 |
| 4,338,930 | 7/1982 | Williams .................. 128/200.26 |
| 4,344,428 | 8/1982 | Sherman .................. 128/12 |
| 4,363,320 | 12/1982 | Kossove .................. 128/200.26 |
| 4,425,911 | 1/1984 | Luomanen . |

FOREIGN PATENT DOCUMENTS

| | | | |
|---|---|---|---|
| 1166977 | 4/1964 | Fed. Rep. of Germany .................. | 128/200.26 |
| 83331 | 6/1964 | France .................. | 128/200.26 |
| 1348516 | 12/1964 | France .................. | 128/200.26 |
| 23003 | 4/1962 | German Democratic Rep. .................. | 128/206.29 |

Primary Examiner—Edward M. Coven
Assistant Examiner—K. M. Reichle
Attorney, Agent, or Firm—Browdy and Neimark

[57] ABSTRACT

An airway for insertion into the mouth to provide a passage for air or anaesthetic gas into the trachea. In order to prevent damage to the teeth of the patient which can occur owing to involuntary clamping of the jaw during anaesthesia, the airway is adapted to hold the mouth open to prevent excessive force being exerted between the upper and lower front teeth. In the described embodiment, the airway has bracing portions in the form of two-section tubes (14) adapted to fit between the upper and lower molar teeth on each side of the mouth, the tubes also providing part of the passage for air or gas. The bracing tubes (14) are connected to a third tube (12) which is curved so as to extend into the oraphayngeal space. The airway may be formed in one piece from plastics material, and may be reusable or disposable.

6 Claims, 2 Drawing Sheets

AIRWAY

This application is a continuation of application Ser. No. 930,054, filed 9/18/85, now abandoned.

Field of the Invention

That application is a continuation of application Ser. No. 778,181, filed Sept. 18, 1985, now abandoned.

This invention relates to airways for insertion into the mouth to provide a passage for air or gas into the trachea.

Description of the Prior Art

Known airways for use in anaesthesia consist of a tube which is inserted into the mouth to provide a passage for air or gas and to hold down the tongue to prevent it falling into the ora-pharyngeal space.

A problem which can occur during anaesthesia arises from the fact that the anaesthetic agents used can cause the patient's jaws to be clamped together with considerable force. Clamping together of the front teeth, which have a shearing action, causes lateral force to be applied to the teeth, and the force can be sufficient to cause damage to the teeth, particularly if one or more front teeth are fitted with artificial crowns.

Object of the Invention

It is an object of this invention to provide an airway which, in addition to providing a passage for air or gas, can protect the teeth from damage due to involuntary clamping of the jaws.

Summary of the Invention

This invention consists in an airway for insertion into the mouth to provide a passage for air or anaesthetic gas into the trachea, in which the airway is adapted to hold the mouth open to prevent excessive force being exerted between the upper and lower front teeth.

Preferably, the airway has bracing portions adapted to fit between the upper and lower molar teeth on each side of the mouth to prevent engagement between the upper and lower front teeth.

In one form of the invention, the bracing portions comprise two tubes providing part of the passage for air or gas, the tubes being connected at their rear ends to a third tube shaped to extend into the ora-pharyngeal space.

The airway may be formed in one piece from plastics such as nylon. It can therefore be made inexpensively.

Brief Description of the Drawings

The invention will now be described, by way of example with reference to the accompanying drawings, in which.

Detailed Description of the Preferred Embodiments

Figure 1:
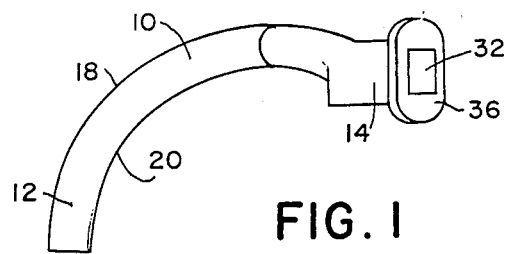
FIG. 1 is a side elevation of an airway in accordance with the invention.
Figure 2:
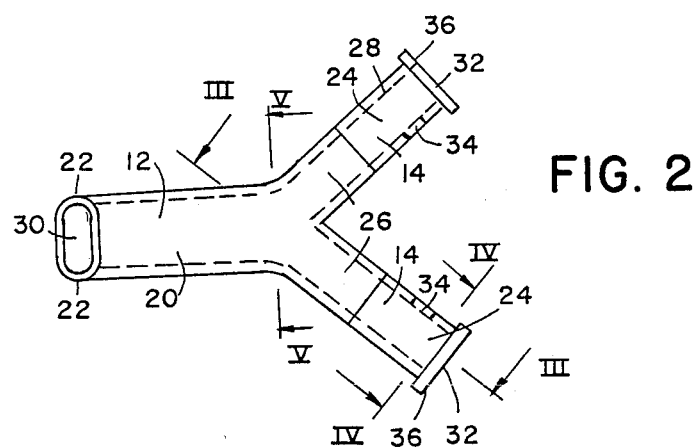
FIG. 2 is an underneath plan view of the device.
Figure 3:
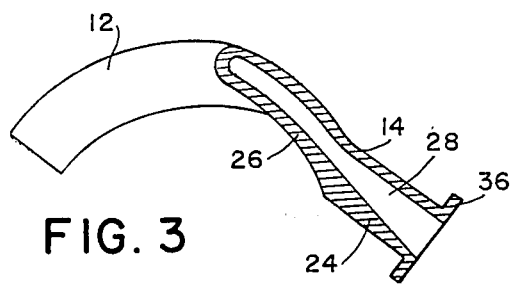
FIG. 3 is a section on line III—III of FIG. 2.
Figure 4:
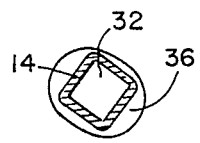
FIG. 4 is a section on line IV—IV of FIG. 2.
Figure 5:
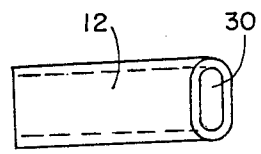
FIG. 5 is a section on line V—V of FIG. 2.

Referring to the drawings, the airway 10 consists of a curved tube 12 joined to two bracing tubes 14.

The curved tube 12 extends along an arc of a circle through 90° from its junction with the branch tubes 14. In cross-section the curved tube 12 has flat upper and lower walls 18 and 20 joined by curved side walls 22. In the illustrated embodiment the curved tube has a outside width of 19 mm, an outside depth of 10 mm and a wall thickness of 2 mm, and extends through an arc with a radius of curvature (measured at the centre line of the tube) of 46 mm.

The bracing tubes 14 extend from the junction with the curved tube 12, at an angle of about 80° with one another, so that the device is generally Y-shaped in plan view. Each bracing tube 14 has a straight portion 24, generally separate in cross-section, joined to the curved tube 12 by a curved portion 26 which merges smoothly into the curved tube 12. The bore 28 in each bracing tube 14 is connected to the bore 30 in the curved tube 12. Near the mouth 32 of each bracing tube 14 a hole 34 is formed in the wall of the tube, on the side facing the other bracing tube 14. The mouth 32 of each bracing tube 14 is surmounted by an outwardly extending lip 36, having a generally elliptical shape.

In the illustrated embodiment, each bracing tube 14 has an outside width and depth of 14 mm and a length of about 50 mm.

The airway may be formed in one piece, for example by injection moulding of a rigid plastics such as nylon.

Figure 6:
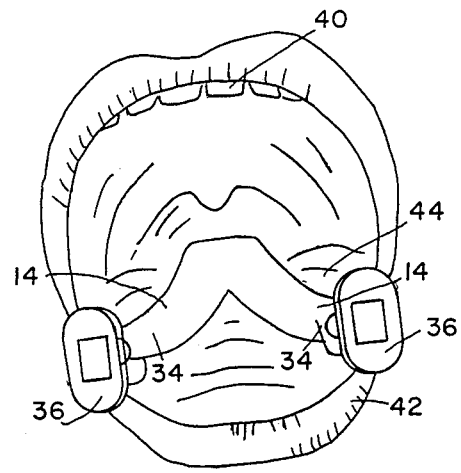
FIG. 6 is a diagrammatic front view showing the device in position in the mouth of a patient, with the patient's mouth open.
Figure 7:
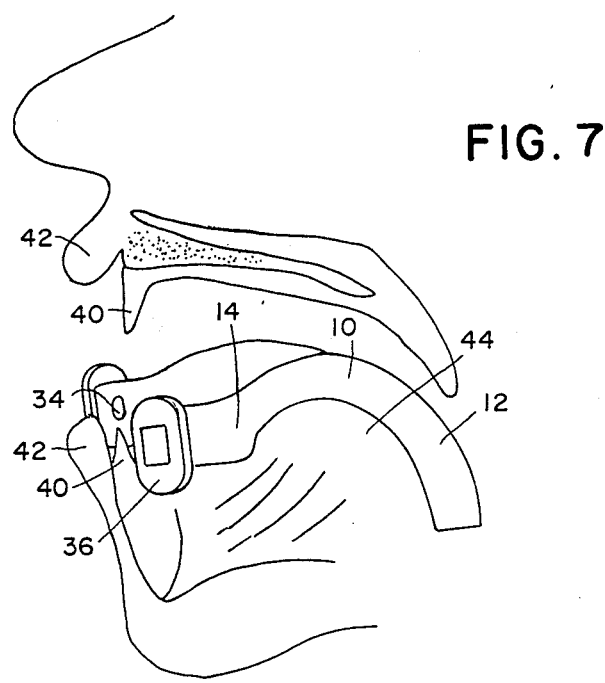
FIG. 7 is a diagrammatic side view of the device in position in the mouth.

In use, the airway 10 is inserted into the patient's mouth, as shown in FIGS 6 and 7, so that the curved tube 14 extends into the ora-pharyngeal space and the bracing tubes 14 rest on the lower molar teeth. When the mouth is closed the bracing tubes 14 are gripped between the upper and lower molar teeth, and act as a brace to prevent the mouth closing completely, and to prevent engagement between the upper and lower front teeth 40 of the patient.

The curved tube 12 holds down the patient's tongue 44 to prevent it falling into the ora-pharyngeal space. The lip 36 at the end of each bracing tube 14 prevents the patient's lips 42 from closing over the mouths of the tubes. The airway thus ensures that there is a free passage for air or anaesthetic gas through the bores 28 and 30 of the tubes 12 and 14 to the patient's lungs. Since the patient's mouth is held open, the device also enables air or gas to flow around the bracing tubes 14. The holes 34 in the side walls of the bracing tubes 14 ensure that gas can enter the tubes even if the mouths 32 of the tubes 14 are occluded by an anaesthetic face mask.

The device thus prevents the danger of damage to the patient's front teeth, whilst providing a passage for the supply of air or gas to the patient's lungs.

The airway may be manufactured inexpensively, and may be provided either in reusable or disposable form.

The airway of this invention could be used in other applications, apart from its use in anaesthetic procedures, for example in preventing damage to the teeth where involuntary clamping may occur, for instance in electro-convulsive therapy.

It will be appreciated that the airway of this invention could take forms other than that of the embodiment shown in the drawings. For example, the device may have braces for interposition between some or all of the teeth to prevent damage to the teeth, with one or more separate tubes to provide the air or gas passage. The device could be made in a variety of materials. An advantage of the embodiment shown in the drawings, however, is that the front teeth need not contact the airway, as the bracing portions rest squarely on the molars. Thus, possible damage to the front teeth by contact with the airway, as well as by collision between the top and bottom front teeth, is prevented.

I claim:

1. An airway for insertion into the mouth of a subject, and for defining a passage for air or anaesthetic gas into the trachea of the subject, comprising:
   (a) first and second tubes each having a forward end and a rear end;
   (b) the first and second tubes being joined at their rear ends to define an intersection, said first and second tubes also being joined at said intersection to a third tube, and said first and second tubes being inclined to one another and to the third tube, said first and second tubes being otherwise spaced apart from each other, the spacing between said tubes increasing from said intersection to said forward ends, said first, second and third tubes thus defining a structure in a configuration which is Y-shaped in plan view;
   (c) the third tube being shaped to extend into the orapharyngeal space of the subject;
   (d) each of the first and second tubes having a bore which extends from its forward end to its rear end, and the third tube having a bore which is connected to the bores in the first and second tubes, the bores in the first, second and third tubes forming a passage for air or anaesthetic gas;
   (e) each of the first and second tubes having a straight bracing portion extending rearward from its forward end and a rear portion connecting the bracing portion to the third tube, said spacing between said first and second tubes being such that said bracing portions and their associated bores are positioned for being gripped in use between upper and lower molar teeth of the subject on respective opposite sides of the mouth of the subject so that said forward ends of said first and second tubes face outward from the mouth, thereby to hold the mouth open to prevent engagement between upper and lower front teeth of said subject and wherein said airway is free of connections extending between said first and second tubes forward of said intersection to prevent engagement between said airway and said upper and lower front teeth.

2. An airway as claimed in claim 1, in which each of said first and second tubes has formed at its forward end a laterally extending lip.

3. An airway as claimed in claim 1, in which each of said first and second tubes has formed adjacent its forward end at least one aperture in its wall, communicating with the bore of the respective tube.

4. An airway as claimed in claim 1, in which said airway is formed in one piece from rigid plastics.

5. The airway of claim 1, wherein said bracing portions are formed of rigid plastic.

6. The airway of claim 1, wherein said bracing portions have outside heights greater than the outside heights of the rear section of said first and second tubes.

* * * * *